United States Patent

Zippel et al.

[11] Patent Number: 5,540,686
[45] Date of Patent: Jul. 30, 1996

[54] APPARATUS FOR LENGTHENING BONES

[75] Inventors: Hartmut Zippel; Karsten Lang, both of Berlin, Germany

[73] Assignee: Endocare AG, Switzerland

[21] Appl. No.: 318,759

[22] PCT Filed: Feb. 16, 1994

[86] PCT No.: PCT/EP94/00445

§ 371 Date: Oct. 14, 1994

§ 102(e) Date: Oct. 14, 1994

[87] PCT Pub. No.: WO94/18898

PCT Pub. Date: Sep. 1, 1994

[30] Foreign Application Priority Data

Feb. 18, 1993 [DE] Germany ............ 43 05 047.6

[51] Int. Cl.$^6$ .................................. A61B 17/66
[52] U.S. Cl. .................. 606/56; 606/57; 606/59
[58] Field of Search .................. 606/54, 55, 56, 606/57, 58, 59, 72, 73, 103

[56] References Cited

U.S. PATENT DOCUMENTS

| | | | |
|---|---|---|---|
| 2,055,024 | 9/1936 | Bittner, Jr. | 606/56 X |
| 3,727,610 | 4/1973 | Riniker | 606/56 X |
| 3,941,123 | 3/1976 | Volkov et al. | 606/56 X |
| 4,338,927 | 7/1982 | Volkov et al. | 606/56 X |
| 4,890,631 | 1/1990 | Hardy | 606/59 |
| 4,973,331 | 11/1990 | Pursley et al. | 606/54 |

FOREIGN PATENT DOCUMENTS

| | | |
|---|---|---|
| 0194187 | 9/1986 | European Pat. Off. . |
| 2129735 | 10/1972 | France . |
| 3345276 | 8/1984 | Germany . |
| 3802743 | 8/1989 | Germany . |
| 2114891 | 9/1983 | United Kingdom . |
| 8805288 | 7/1988 | WIPO . |

*Primary Examiner*—Guy Tucker
*Attorney, Agent, or Firm*—Andrus, Sceales, Starke & Sawall

[57] ABSTRACT

An apparatus for lengthening bones is disclosed including a plurality of frame elements (12) spaced apart from one another. The frame elements are U-shaped for at least partially enclosing the bone, and two elements may be connected to fully enclose the bone. Fixation elements (14) that transfix the bone approximately perpendicular to its long direction are secured to the frame elements. Telescopically extendable tensioning elements (16) connect the frame elements together and fix them in position relative to one another. The frame elements (12) include a plurality of rows (18, 18') of longitudinal slots (20, 20', 20"). The tensioning elements (16) are clamped to the frame elements at aligned slots and the fixation elements (14) are similarly clamped to the appropriate slots in the corresponding frame elements. The tensioning elements include three threaded sections with a first section including a spindle and sleeve with a second and third threaded section threaded into the first section. The second and third sections form part of a threaded rod which is a single continuation rod or a rod having a center pivot joint.

26 Claims, 6 Drawing Sheets

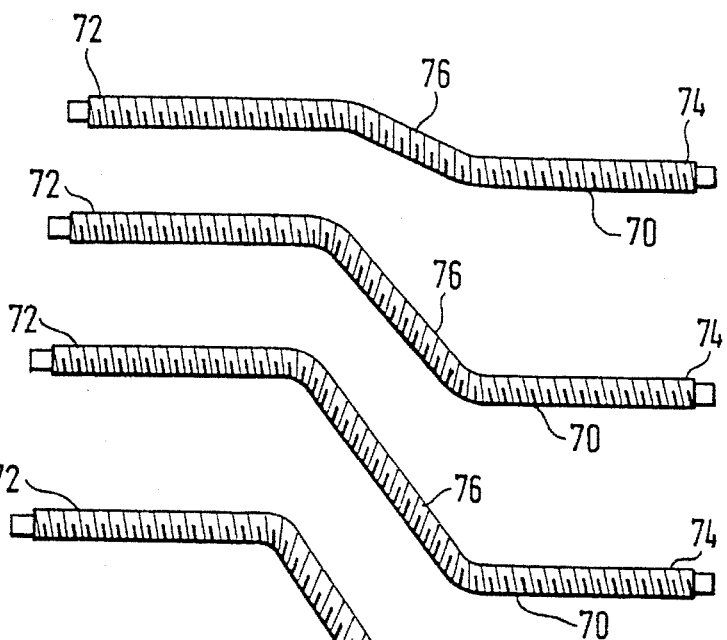
FIG. 9A
FIG. 9B
FIG. 9C
FIG. 9D
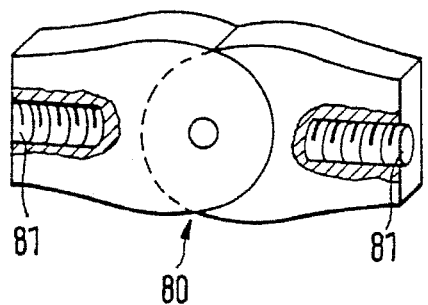
FIG. 10C
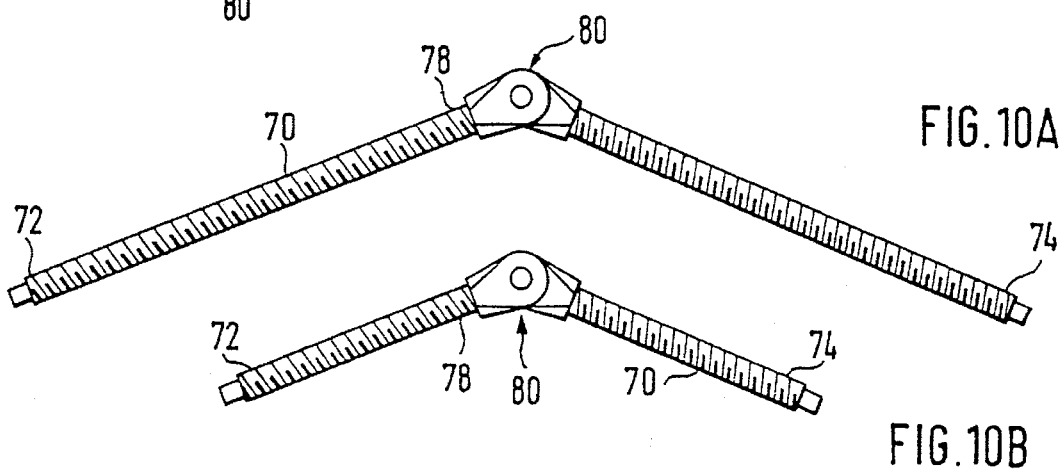
FIG. 10A
FIG. 10B

APPARATUS FOR LENGTHENING BONES

BACKGROUND OF THE PRESENT INVENTION

This is a 35 U.S.C. 371 application based on PCT/US94/00445, filed Feb. 16, 1994.

The invention relates to an apparatus for lengthening bones.

Apparatuses of this kind, which not only lengthen bones but in addition serve to transport bone fragments within part of a limb, to restore the mobility of joints, to correct congenital or acquired axial misalignments of the limbs, to treat fresh or slowly healing bone fractures, to aid the healing of artificial joints and to stiffen joints by acting as an external stabilizer or fixator, are sufficiently well known. Each such apparatus for lengthening bones comprises at least two frame elements at a distance from one another, which at least partly enclose the bone, to receive and fasten both fixation elements and tensioning elements or the like. The fixation elements, which transfer force to the bone and take the form of wires such as Kirschner wires, screws, Schanz's screws etc., transfix the bone about perpendicularly to its long direction or are drilled into and/or through the bone under aseptic, sterile conditions and fixed to the external frame elements. The tensioning elements or the like, which can be extended telescopically and which connect the frame elements to one another and establish their relative positions, are provided to produce controllable and continuous tractive and pressure forces to lengthen bones, treat bone fractures, and mobilize or stabilize joints.

All these apparatuses present the disadvantage of decidedly elaborate construction. For example, their frame elements are generally constructed as closed rings provided with a single row of holes to receive and fasten the fixation elements on the one hand and the tensioning elements or the like on the other hand. Apart from the fact that such closed rings are not needed in the treatment of every case, they complicate the manipulation of the whole apparatus, particularly for placement and removal during the surgical operation. Furthermore, such closed rings prevent direct access to the bone concerned. In addition, the arrangement of the fixation elements and tensioning elements or the like at each of the frame elements is largely predetermined by the single row of holes, so that it cannot be altered as desired. As another example, the tensioning elements or the like in these apparatuses are in many cases formed by a threaded sleeve with two threaded rods, one at each of its ends, which can be screwed into the threaded sleeve. By rotation of the threaded sleeve, in many cases both of the threaded rods fastened to the associated frame element are simultaneously lengthened or shortened. With this arrangement, fine adjustment of the distance between the frame elements is very difficult. Moreover, the threaded sleeve in such an apparatus has a fixed, unalterable length, so that a tensioning element or the like intended for a relatively short distance between the associated frame elements cannot be used for a larger distance between the associated frame elements. Such tensioning elements or the like, and hence these apparatuses, cannot be employed in a versatile manner when it is desired to vary the distance between the frame elements, unless the tensioning elements or the like are exchanged for others of different length.

Not the least result of these disadvantages is that manipulation of these apparatuses is relatively difficult, both during the operation phase and during the subsequent healing phase.

Finally, in practice such apparatuses have additionally proved to be very heavy, which severely affects acceptance by the patient.

SUMMARY OF THE PRESENT INVENTION

The present invention is directed to the problem of providing an apparatus for lengthening bones of the generic kind that is decidedly simple and light-weight in construction and especially simple to manipulate.

This problem is generally solved in accordance with the invention by frame elements which are each U-shaped, semi-oval or the like and comprise at least one row, and preferably two or more rows, of longitudinal slots for attaching the fixation elements and tensioning elements.

Owing to the shape of the frame elements in accordance with the invention, an apparatus for lengthening bones, for medical therapy etc. is provided which can be used by orthopedists, traumatologists and reconstructive surgeons at all parts of the upper and lower extremities, and which altogether is extremely simple with respect to its construction and manipulation during both the operation phase and the healing phase.

That is, the semi-oval frame elements allow maximally undisturbed access to the bone or the operation area. As a result, the surgeon's work during the operation itself is greatly facilitated. During the healing phase, too, the surgeon can undertake corrective measures with very little difficulty. So that the semi-oval frame elements can be individually adapted to the diameter or circumference of the individual bone or the patient's limb, thereby making the frame more comfortable to wear, the semi-oval frame elements can be of different sizes.

Furthermore, the provision of slots in the frame elements allows any desired arrangement of both the fixation elements, which transfer force to the bone, and the tensioning elements or the like. The apparatus for lengthening bones in accordance with the invention is thus useful in diverse applications and/or can be adapted to the particular circumstances of the individual, both for attaching the fixation elements in the form of wires, screws or the like to each frame element on the one hand, and for fixing the tensioning elements etc. of the frame elements with respect to one another on the other hand. Thus additional rotational corrections can be undertaken throughout the treatment. Finally, the frame elements in accordance with the invention can also readily be arranged to form a complete oval ring, which increases the resistance to torsion of the whole apparatus for lengthening bones in accordance with the invention.

Further in another construction, the longitudinal slots in two neighboring rows of longitudinal slots are so disposed that they overlap. In this way the frame element according to the invention is provided with at least one quasi-continuous slot, so that the fixation elements and tensioning elements can be positioned as desired at each frame element, depending on the individual features of the bone or the limb including, for example, the courses of nerves, arteries and veins. The distance to the two adjacent fixation elements and/or tensioning elements can also thereby be reduced to a minimum.

It is further within the scope of the invention, to interrupt the rows of longitudinal slots by at least one transverse slot, to angle at least one longitudinal slot in a row of longitudinal slots so that one end slants toward a neighboring row of longitudinal slots, and to make at least one longitudinal slot in a row of longitudinal slots at the end of the semi-oval frame element freely accessible at the end face. In this way the manipulability of the semi-oval frame element, and hence that of the entire apparatus for lengthening bones etc. in accordance with the invention, is improved and the range of possible applications of both is additionally increased.

Of particular interest for further simplifying the manipulation of the apparatus for lengthening bones etc. in accordance with the invention are the additional characteristics which are also independent of other features include attachment bolts that can be clamped to the frame elements in order to receive and fasten the fixation elements. Here the fixation elements, which transfer force to the bone, have the form of wires such as Kirschner wires which are fastened crosswise in bores made through the bone or limb while taking into account the anatomical courses of nerves and vessels.

It is also advantageous for the attachment bolts that clamp the Kirschner wires to bear on the frame element over a large surface, to ensure rotational stability. As a result of such large-area contact, the frictional force acting between the individual attachment bolt and the associated frame element is increased. It is therefore unnecessary to fix the attachment bolt by a locknut as it is tightened.

It is further within the scope of the invention, to construct the attachment bolts in two parts. The one part comprises a bolt head and a screw thread, between which is disposed a section with a bore, preferably a central bore, to receive the Kirschner wire. The diameter of the bore section is smaller than that of the bolt head, but larger than the diameter of the screw thread. The other part amounts to a clamp washer or the like, with one side that faces the bolt head and contacts the Kirschner wire and another side that faces away from the bolt head and lies flat on the frame element. The one side of the clamp washer or the like thus bears on and anchors the Kirschner wire, which having been received by the bore lies directly below the bolt head, whereas the other side makes contact over a large area with the frame element.

A further characteristic wherein a clamp washer is used including having the clamp washer or the like having an aperture corresponding in size to the bore section and receiving the latter. This structure additionally provides stable and permanent anchoring of the Kirschner wire within the attachment bolt and hence to the frame element.

In a particular construction, the clamp washer or the like is provided on its side facing the bolt head, with at least two diametrically opposed, radially oriented notches, grooves or the like, which receive at least in part the Kirschner wire passing through the bore section of the attachment bolt. As a result, bending or even breakage of the associated Kirschner wire is prevented, even when excessive force is applied to tighten the nuts on the attachment bolt.

The attachment bolts are also advantageously each fixed with a nut incorporating a disk or the like that bears on the frame element and is slightly tiltable. By constructing the nuts in this way, manipulation of the apparatus for lengthening bones as a whole is simplified, especially during the operation, and in addition the entire screw connection is endowed with high mechanical stability.

Of great significance in further simplifying the manipulability of the apparatus for lengthening bones etc. in accordance with the invention are the independent structural characteristics in the structure of telescopically extendable tensioning elements or the like, which connect the frame elements together and fix them in position relative to one another. The tensioning elements includes at least two, preferably three threaded sections that interlock with one another at least partially. This allows particularly exact fine adjustment and, in addition, both small and large distances between individual frame elements can be obtained with the same tensioning elements or the like, according to the particular surgical requirements, with no need to exchange individual tensioning elements for tensioning elements of different length during the operation phase, but especially during the treatment and healing phase. Being adjustable in length, even over a large range, these tensioning elements or the like are extremely versatile in use and, therefore, so is the whole apparatus for lengthening bones, etc. in accordance with the invention.

According to another characteristic of the tensioning elements which can be provided is, a first threaded section which consists of a central threaded spindle and a central threaded sleeve that cooperates with the threaded spindle, into which, by way of their opposite ends, can be screwed a second and a third threaded section.

In further development of the invention, the thread of the first threaded section turns in the opposite direction to those of the second and the third threaded section. In a particular structure, the first threaded section has a left-handed thread and both the second and third threaded sections are right-handed. In this way the tensioning elements or the like can expand by at least twice the length of the first threaded section, so that no exchanging of particular tensioning elements or the like is required during the treatment.

Owing to the other features in which the first threaded section is equipped with a marker—in particular, the central threaded spindle is provided in the median longitudinal direction with a groove, notch or the like, while the threaded sleeve is provided in the vicinity of its opening with a circumferentially arranged scale or the like—it is possible to extend the associated tensioning element in a precisely predetermined, accurately measured manner.

It is also advantageous, according to Claim 18, for the second and third threaded sections each to be constructed as a threaded rod.

In the further aspect within the scope of the invention the two ends of the threaded rod are coaxial with the long axis of the threaded rod. It should be mentioned in this regard that the frame elements can be connected together and fixed with respect to one another by means of threaded rods of different lengths.

In an alternative form of the invention the two ends of the threaded rod can equally well be oriented in parallel to one another, which enables parts of the frame differing in size and/or diameter to be effortlessly connected to one another or assembled. In this case, according to a further structure the threaded rod is bent to form a middle region disposed at an angle of up to 90° with respect to the two ends of the threaded rod.

The two ends of the threaded rod can enclose an angle of up to 180°. The threaded rod may include a middle region within which a hinge-like joint or the like is disposed. Such a threaded rod is employed mainly for apparatuses for lengthening bones or extremities that extend across joints, or when axis corrections are intended. Such a threaded rod with a hinge-like joint can be arranged in so many configurations that it allows corrections with all degrees of freedom.

Every straight threaded rod, bent threaded rod or threaded rod with hinge-like joint can be anchored to the associated frame elements by its ends, in each case by means of a nut incorporating a slightly tiltable disk or the like that rests against the frame element, to simplify manipulation of the apparatus in accordance with the invention and to increase its mechanical stability.

Moreover, the second and third threaded sections can also be attached to the associated frame element so that they are at an angle to that frame element. In this way axial deviations of the bones or limbs can be compensated. It has proved particularly advantageous in this respect, for the second and third threaded sections to be attached to the associated frame element by way of a nut with a dome shape on the side toward the frame element and a machined washer with a matching concave bearing surface, corresponding to the dome shape of the nut, on the side away from the frame element. As a result, the second and third threaded sections can be fixed by their ends at an angle to the horizontal of about 45°, in particular ca. 30°.

Finally, the frame elements and/or the tensioning elements and/or the attachment bolts consist, according to one feature maybe aluminum, in particular of duralumin. The consequence is an apparatus for lengthening bones or limbs with decidedly low weight and, concomitantly, a high degree of patient acceptance.

BRIEF DESCRIPTION OF THE DRAWINGS

Additional characteristics, advantages and details of the invention will become apparent in the following description of some preferred embodiments of the invention, with reference to the drawings, wherein:

FIGS. 9A, 9B, 9C and 9D are schematic plan views of embodiments of a second and/or third threaded section constructed in accordance with the invention;

FIGS. 10A and 10B are schematic plan views of other embodiments of a second and/or third threaded section constructed in accordance with the invention;

FIG. 10C is a perspective view of another embodiment of a hinge-like joint constructed in accordance with the invention;

DESCRIPTION OF THE ILLUSTRATED EMBODIMENT

Figure 1:
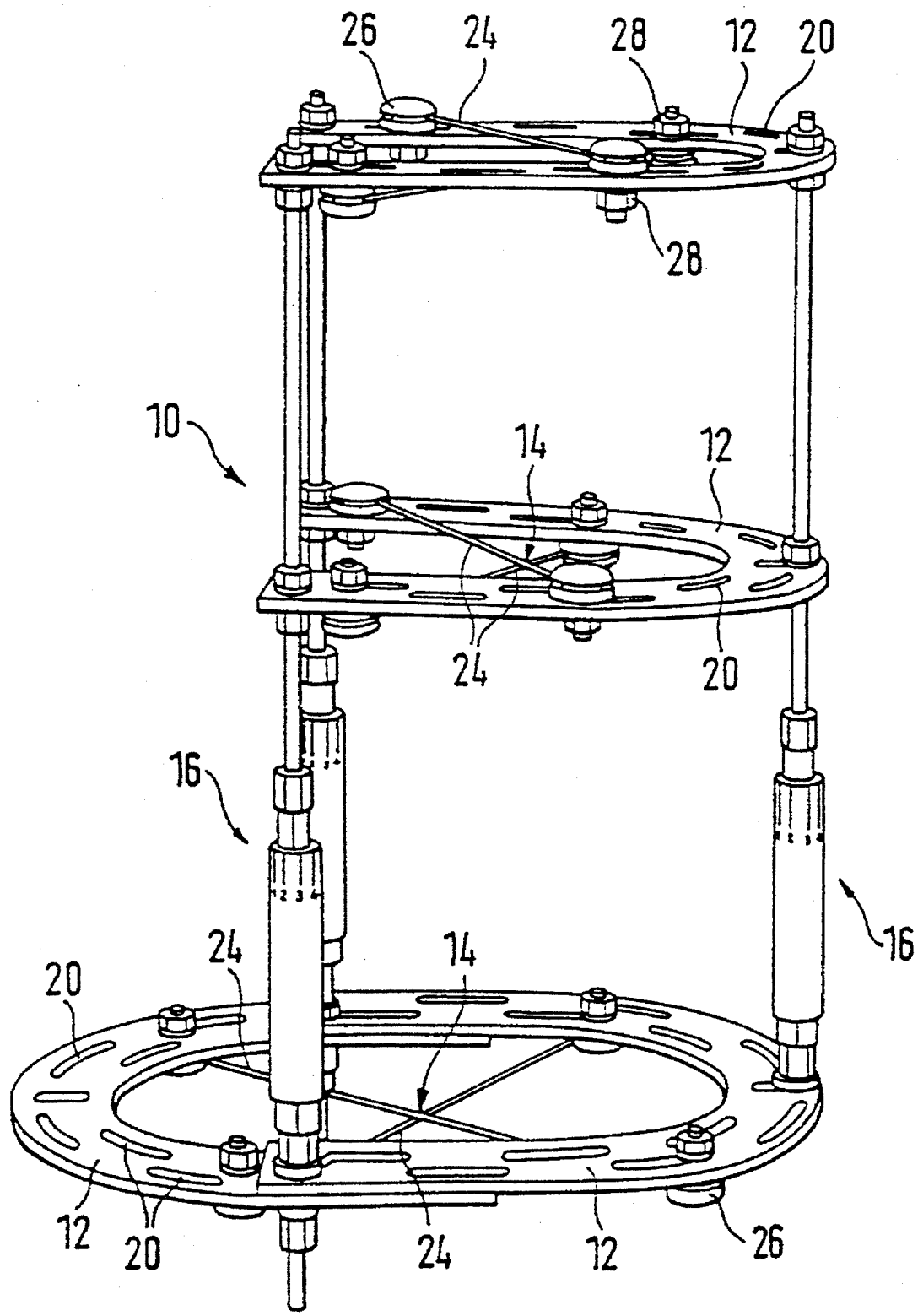
FIG. 1 is a perspective side view of an embodiment of an apparatus for lengthening bones in accordance with the invention.

The embodiment of an apparatus 10 for lengthening bones or limbs etc. shown in FIG. 1 comprises a total of four frame elements 12, spaced apart from one another and enclosing the associated bone (not illustrated) at least partially, in the case of the two upper frame elements 12, or completely, in the case of the bottom two frame elements 12. The frame elements 12 are provided to receive and fasten fixation elements 14 on the one hand and tensioning elements 16 or the like on the other hand.

Figure 2:
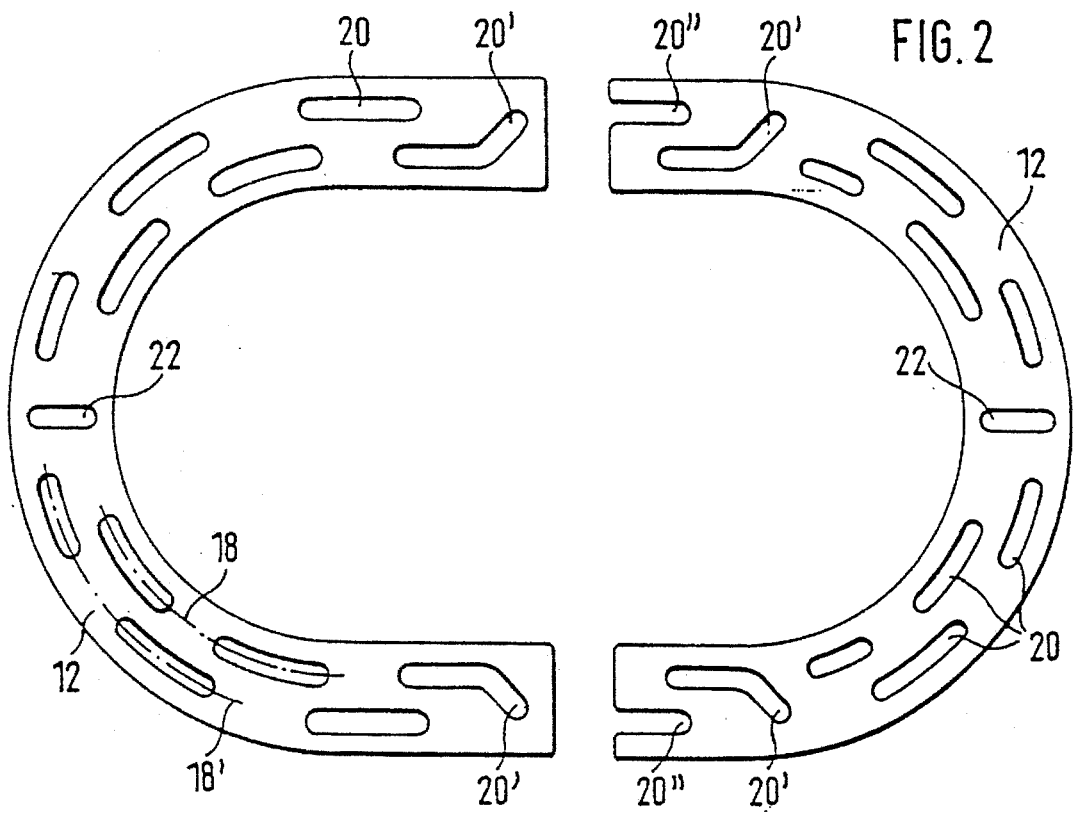
FIG. 2 is a plan view of two embodiments of semi-oval frame elements constructed in accordance with the invention, enlarged.
Figure 3:
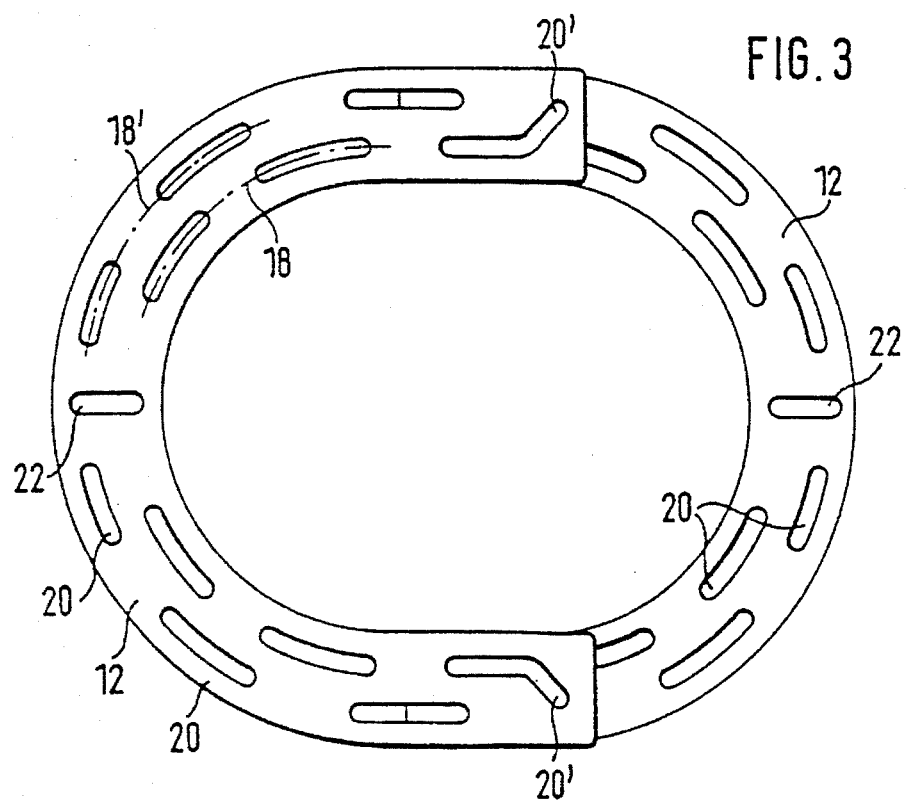
FIG. 3 is a plan view of an oval formed by the two semi-oval frame elements according to FIG. 2.

As shown in FIGS. 1 to 3, each of the frame elements 12 is U-shaped, semi-oval or the like. This shape permits nearly unimpeded access to the operation area during surgery and thus facilitates the surgeon's manipulations. Furthermore, as shown in FIGS. 1 and 3, pairs of U-shaped, semi-oval or similar frame elements can be put together without difficulty, during the operation or during the subsequent actual treatment, to form a complete oval or circular ring etc., which simultaneously increases the torsional rigidity of the assembled apparatus 10 for lengthening bones or limbs.

The frame elements 12 in addition comprise at least one, preferably two-as illustrated in FIGS. 1 to 3—or several rows 18, 18' of longitudinal slots 20, 20', 20". The longitudinal slots 20, 20', 20" serve to fasten the fixation elements 14 and tensioning elements 16 to the frame elements 12. The longitudinal slots 20, 20', 20" in the two adjacent rows 18, 18' of longitudinal slots 20, 20', 20" are arranged so as to overlap one another. The amount of overlap, as shown in FIGS. 2 and 3, is about equal to the width of each longitudinal slot 20, 20', 20". Because of these overlapping longitudinal slots 20, 20', 20", the apparatus 10 for lengthening bones can be employed for a greater variety of applications and is more flexibly manipulable.

In the frame elements 12 according to FIGS. 2 and 3 the rows 18, 18' of longitudinal slots 20, 20', 20" are interrupted by at least one transverse slot 22. In addition, at least one longitudinal slot 20' in the row 18 of longitudinal slots 20, 20' is angled so that one end slants toward the adjacent row 18' of longitudinal slots 20, 20" Finally, at least one longitudinal slot 20" in the row 18' of longitudinal slots 20, 20" at the end of the U-shaped, semi-oval or similar frame element 12 is freely accessible from the end face, so that it corresponds to a recess. Because the longitudinal slots 20, 20', 20" in the frame element 12 are so constructed, a greater degree of variation is provided for the attachment of fixation elements 14 and tensioning elements 16 to the associated frame element 12.

As is clearly evident in FIG. 1 the fixation elements 14, which transfer force to the bone, have the form of wires such as Kirschher wires 24, screws, Schanz's screws or the like, which under aseptic sterile conditions are drilled into or through the bone or the limb so as to transfix the bone approximately perpendicular to its long direction, and are subsequently attached to the associated frame element 12.

To receive and hold firm the fixation elements 14 in the form of Kirschner wires 24, attachment bolts 26 that can be clamped to the frame elements 12 are provided. The attachment bolts 26 are each constructed so that the attachment bolts 26 for the Kirschner wires 24 bear on the frame element 12 over a large area. This arrangement makes the attachment bolts 26 rotationally stable, so that to tighten them by means of a nut all that is needed is an open-end wrench, ring wrench etc. applied exclusively to the nut 28.

Figure 5:
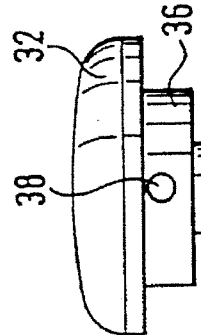
FIG. 5 is a side view of the attachment bolt in accordance with the invention shown in FIG. 4, on a smaller scale.
Figure 6:
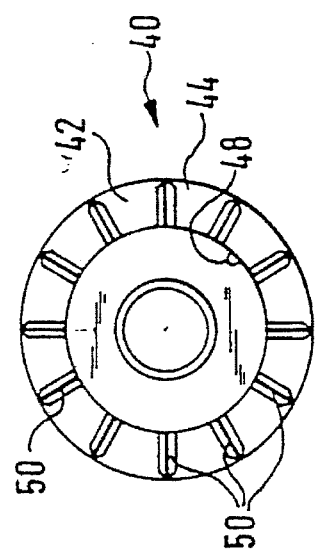
FIG. 6 is a perspective view from above of the clamp washer in accordance with the invention shown in FIG. 4 as indicated by arrow VI, on a smaller scale.
Figure 4:
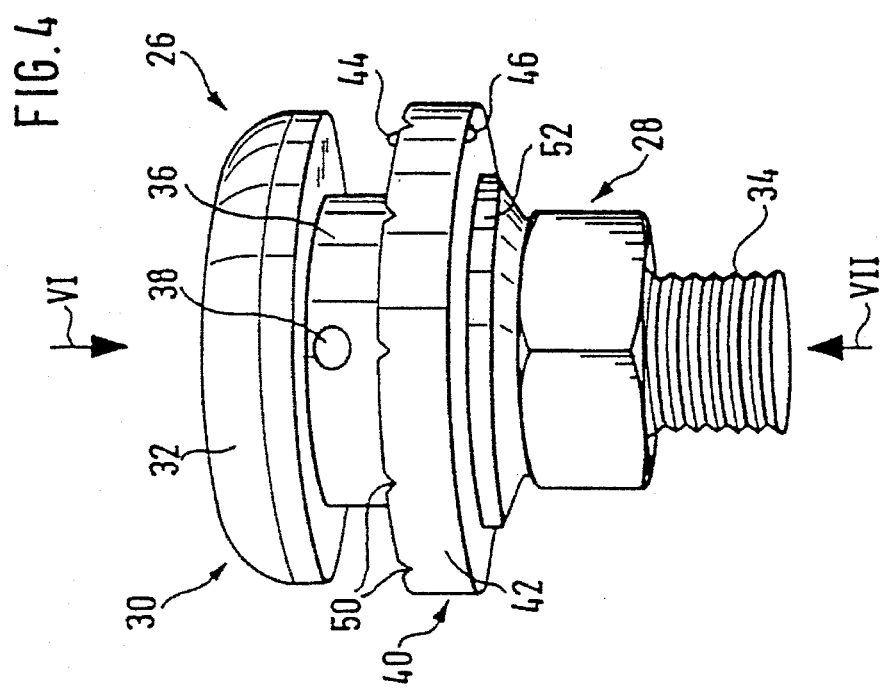
FIG. 4 is a perspective side view of an embodiment of an attachment bolt constructed in accordance with the invention, with a clamp washer and nut in accordance with the invention.

The attachment bolts 26 shown in FIGS. 4 to 6 are constructed in two parts.

The one part 30 comprises a bolt head 32 and a screw thread 34. Between the bolt head 32 and screw thread 34 is disposed a bore section 36 provided with a bore, preferably a central bore 38, to receive the Kirschner wire 24 (not shown). The bore section 36 itself has a diameter smaller than that of the bolt head 32 and larger than the diameter of the screw thread 34.

The other part 40 amounts to a clamp washer 42 or the like. The clamp washer 42 bears on the Kirschner wire 24 by way of a side 44 that faces the bolt head 32, and makes large-area contact with the frame element 12 by way of its other side 46, which faces away from the bolt head 32. The clamp washer 42 or the like includes an aperture 48 corresponding to the bore section 36, which receives the bore section 36. In addition, the clamp washer 42 or the like is provided on its side 44 facing the bolt head 32 with a plurality of notches 50, grooves or the like, diametrically opposite one another and radially oriented, which serve to receive partially the Kirschner wire 24 passing through the bore section 36 by way of the bore 38.

Figure 7:
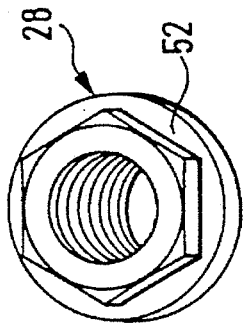
FIG. 7 is a perspective view from below of the nut in accordance with the invention shown in FIG. 4 as indicated by arrow VII, on a smaller scale.

As shown in FIGS. 4 and 7, the attachment bolts 26 can each be clamped in place with a nut 28. The nut 28 incorporates a disk 52, washer or the like, which can be brought into contact with the frame element 12.

Figure 8:
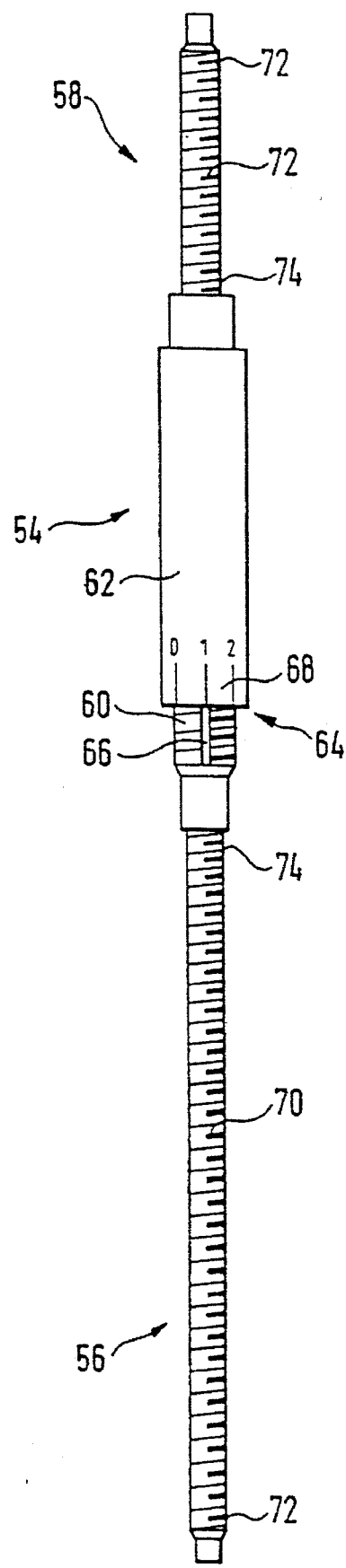
FIG. 8 is a side view of an embodiment of a tensioning element or the like constructed in accordance with the invention, enlarged.

The tensioning elements 16 or the like, as shown in FIGS. 1 and 8, are telescopically extendable, connect the frame elements 12 together and fix the positions of the frame elements 12 with respect to one another. Each tensioning element 16 or the like according to FIG. 8 comprises at least two, preferably three threaded sections 54, 56, 58, which interlock with one another at least partially.

The first threaded section 54 consists of a central threaded spindle 60 and a central threaded sleeve 62, which cooperates with the threaded spindle 60. Into one end of the threaded spindle 60 and the opposite end of the threaded sleeve 62 can be screwed the second and third threaded sections 56, 58.

It is advantageous for the first threaded section 54 to be threaded in a direction opposite to that of the second and third threaded section 56, 58. In particular, for the first threaded section 54 a left-handed thread is provided and for the second and the third threaded section 56, 58 a right-handed thread.

The first threaded section 54 is further equipped with a marker 64 so that the associated tensioning element 12 can be lengthened or shortened by a precisely definable distance. For this purpose, the central threaded spindle 60 is provided in the median longitudinal direction with a groove 66, notch or the like, while the threaded sleeve 62 bears in the region of its opening a scale 68 or the like arranged around its circumference.

As is clearly evident in FIG. 8, the second and third threaded sections 56, 58 are each constructed as a threaded rod 70. The two ends 72, 74 of each threaded rod 70 are coaxial with the median long axis of the threaded rod 70.

As shown in FIGS. 9A to 9D, the threaded rods 70 can alternatively be bent, enabling even frame elements 12 of different diameters to be assembled without difficulty. The two ends 72, 74 of the threaded rod 70 in this case are aligned in parallel to one another and the threaded rod 70 includes a middle region 76 that forms an angle of up to 90° with each of the two ends 72, 74 of the threaded rod. The middle region 76 here can also vary in length.

In a further alternative form of the threaded rod 70 according to FIGS. 10A and 10B, its two ends 72, 74 can be angled with respect to one another by as much as 180°. For this purpose the threaded rod 70 includes a middle region 78 in which a hinge-like joint 80 or the like is disposed. Such a threaded rod 70 is primarily applicable to constructions that extend across joints or in planned axis corrections. As shown in FIG. 10C, the hinge-like joint 80 or the like preferably comprises two threaded bores 81, into which can be screwed threaded rods 70 of very diverse construction, as required for the particular surgical situation—that is, straight threaded rods 70 as well as bent threaded rods 70 according to FIGS. 9A to 9D. The resulting versatility further increases the spectrum of applications of the apparatus 10 for lengthening bones or limbs.

Figure 11:
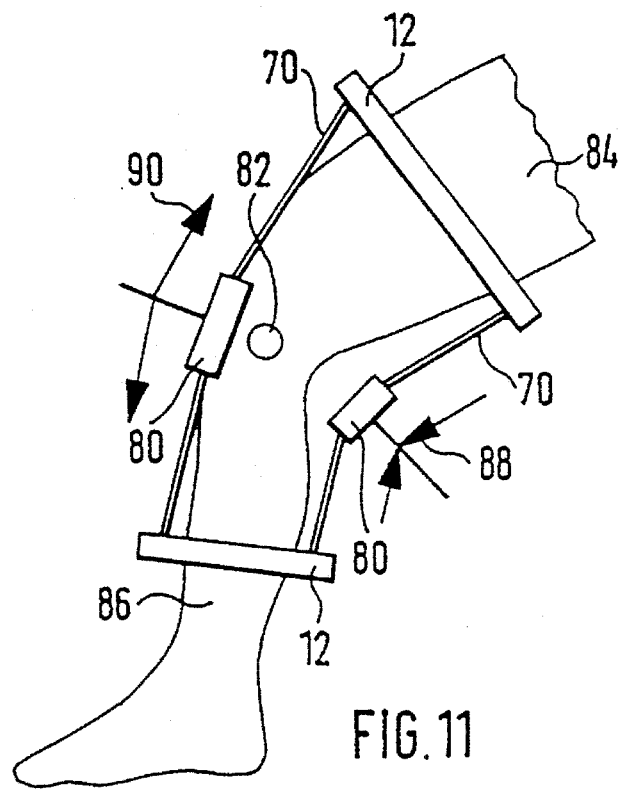
FIG. 11 is a schematic side view of an embodiment of the apparatus in accordance with the invention together with a patient's leg, to illustrate the operation of second and/or third threaded section according to FIGS. 10A and 10B, on a smaller scale.

As shown in FIG. 11, for example, threaded rods 70 according to FIGS. 10A and 10B can be used for the gradual adjustment of the angle of the knee joint 82 shown here, between thigh 84 and shin 86, in that the respective angles enclosed by the two schematically drawn threaded rods 70 between the two frame elements 12 are enlarged. At the same time tensioning elements 16, in particular those according to FIG. 8, can be adjusted in the manner described above, the overall length of the posterior or lower tensioning element 16 with the threaded rods 70 between the two frame elements 12 being shortened and the overall length of the anterior or upper tensioning element 16 with the threaded rods 70 between the two frame elements 12 being lengthened, or vice versa. Thus force is brought to bear on the two frame elements 12, in the posterior region according to double arrow 88 and in the anterior region according to double arrow 90.

Figure 12:
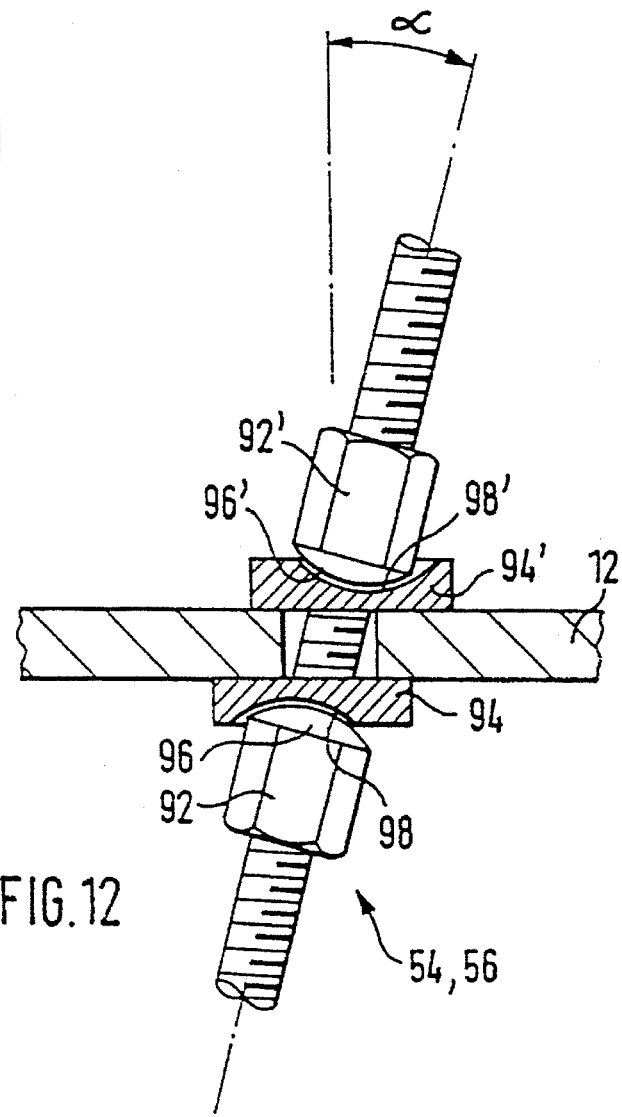
FIG. 12 is a partly cut-away sectional view of an embodiment of a dome-shaped nut with washer in accordance with the invention, for fixing a tensioning element in accordance with the invention at an angle.

According to FIG. 12 the second and third threaded sections 54, 56 can also be attached to the frame element 12 so as to form an angle with the frame element 12. Here the second and third threaded sections 54, 56 are fixed to the associated frame element 12 by way of a nut 92 and a machined washer 94. The nut 92 is dome-shaped in the region 96 facing the frame element 12. The machined washer 94 opposite it has a concave bearing surface that corresponds to the dome-shaped region 96 of the nut 92 but faces away from the frame element 12. The counteracting mechanism by which the second and third threaded sections 54, 56 are fixed in position correspondingly comprises a nut 92' with a dome-shaped region 96' and a machined washer 94' with a concave bearing surface 98'.

The frame elements 12 and/or the tensioning elements 16 and/or the attachment bolts 26, in order to reduce the weight of the apparatus 10 for lengthening bones or limbs, all consist of aluminum and preferably duralumin, which increases the acceptability of the apparatus 10 to the patients.

The present invention is not restricted to the preceding exemplary embodiments. Rather, it is entirely possible instead of the telescopically extendable tensioning elements 16 or the like to insert rigid, i.e. non-extendable threaded rods or the like between the individual frame elements 12 and fasten them thereto. It is equally conceivable to provide rigid, non-extendable threaded rods in addition to the telescopically extendable tensioning elements 16 or the like between the individual frame elements 12, to temporarily enhance the stability of the whole arrangement 10 in accordance with the invention.

All the characteristics disclosed in the application documents are claimed as essential to the invention, to the extent that they are new to the state of the art singly or in combination.

We claim:

1. An apparatus for lengthening bones including at least two frame elements (12) spaced apart from one another and adapted to be mounted enclosing an elongated bone of a patient and having telescopically extendible tensioning elements (16) connected to the frame elements and securing the elements to each other in position relative to one another and having fixation elements (14) adapted to be secured to the frame elements and adapted to transfix the bone of a patient approximately perpendicular to its long direction, the improvement comprising each of said frame elements (12) having a generally U-shaped configuration and having at least two adjacent rows (18, 18') of elongated slots (20, 20', 20"), said fixation elements (14) and said tensioning elements (16) being adapted for securement to said frame elements at said slots, and wherein said elongated slots (20, 20', 20") in said two adjacent rows (18, 18') of elongated slots (20, 20', 20") are arranged to overlap one another.

2. The apparatus according to claim 1, wherein at least one elongated slot (20') in one or more of the rows (18 or 18') of elongated slots (20, 20' 20") is angled so that one end slants toward a neighboring row (18' or 18) of elongated slots (20, 20', 20").

3. The apparatus according to claim 1, including attachment bolts (26) adapted to be clamped to the frame elements (12) and connected to said fixation elements (14) for firmly securing the fixation elements to said frame elements, said fixation elements (14) being constructed as elongated wires (24).

4. The apparatus according to claim 3, wherein the attachment bolts (26) include a head member which substantially overlies the substantially complete width of the frame element and thereby bear on the frame element (12) over a large surface area and hence in a rotationally stable manner.

5. The apparatus according to claim 4, wherein said attachment bolts (26) are constructed in first part (30) and second part (40), the first part (30) comprising a bolt head (32) and bolt rod extending from the head, said rod having a screw thread (34), said first part having a bore section (36) adjacent the bolt head 32 with a bore to receive the elongated wire (24), said bore section (36) having a diameter smaller than that of the bolt head (32) and larger than the diameter of the screw thread (34), and the second part (40) comprising a clamp member (42) abutting said bore section that faces away from the bolt head (32) and contacts the frame element (12) over a large area, said second part having a bore with a diameter smaller with said bore section.

6. The apparatus according to claim 5, wherein said bore section is round and said clamp member is a washer (42) having an aperture (48) that corresponds to the diameter of the bore section (36), and said clamp washer (42) being located with said aperture (48) on said bore section.

7. The apparatus according to claim 5, wherein said clamp washer (42) abutting said bore section having at least two diametrically opposed, radially oriented notches (50) to partially receive one of said wires (24).

8. The apparatus according to claim 5, wherein each attachment bolt (26) receives a nut (28) for fastening the bolt in place, said nut includes a tiltable disk (52) contacting the frame element (12).

9. The apparatus according to claim 1, the improvement further wherein said telescopically extendable tensioning elements (16) comprise at least first and second threaded sections (54, 56, 58) that at least partially interlock with one another.

10. The apparatus according to claim 9, wherein said first threaded section (54) includes a central threaded spindle (60) and a central threaded sleeve (62) threaded onto said spindle, said second threaded section (56) threaded into one end of said spindle and and further comprising a third threaded section (58) threaded into said sleeve.

11. The apparatus according to claim 10, wherein said first threaded section (54) is threaded in the opposite sense to the second and third threaded sections (56, 58).

12. The apparatus according to claim 11, wherein said first threaded section (54) has a left-handed thread and the second and third threaded sections (56, 58) have right-handed threads.

13. The apparatus according to claim 10, wherein the first threaded section (54) includes a marker (64) for the precisely predeterminable lengthening or shortening of the associated tensioning element (16).

14. The apparatus according to claim 13, wherein said marker (64) includes a longitudinal mark on the median longitudinal direction of said central threaded spindle (60), and said threaded sleeve (62) includes a circumferential scale mark (68) on an end portion cooperating with said longitudinal mark.

15. The apparatus according to claim 10, wherein the second and third threaded sections (56, 58) form the opposite end portions (72, 74) of a single threaded rod (70).

16. The apparatus according to claim 15, wherein the two end portions (72, 74) of the threaded rod (70) are coaxial with the median long axis of the threaded rod (70).

17. The apparatus according to claim 15, wherein the two end portions (72, 74) of the threaded rod (70) are oriented in parallel with one another.

18. The apparatus according to claim 17, wherein the threaded rod (70) comprises a middle portion (76) that is set at an angle in a range between substantially greater than 0° and 90° with respect to each of the two end portions (72, 74) of the threaded rod (70).

19. The apparatus according to claim 15, wherein the two end portions (72, 74) of the threaded rod (70) are angled to each other in a range between substantially greater than 0° and 180° with respect to one another.

20. The apparatus according to claim 19, wherein the threaded rod (70) comprises a middle portion (78) including a hinge joint (80).

21. The apparatus according to claim 9, wherein said tension elements included a third threaded section, the second and third threaded sections (54, 56) are adapted to be attached to one of the frame elements (12) and oriented at an angle with respect to the associated frame element (12).

22. The apparatus according to claim 21, having attachment units for attachment of the second and third threaded sections (54, 56) to the frame element (12), each attachment unit includes a nut (92, 92') adapted to be threaded onto the threaded section with a dome-shaped surface facing toward the associated frame element (12) a machined washer (94, 94') located between the nut and the frame element (12) said washer having a concave bearing surface (98, 98') corresponding to the dome-shaped surface of the nut (92, 92') and abutting the dome-shaped surface and the associated frame element (12).

23. The apparatus according to claim 1, the improvement further wherein at least one of the frame elements (12), the tensioning elements (16) and the attachment bolts (26) are made of an aluminum metal.

24. The apparatus according to claim 1, the improvement further wherein said metal is duralumin.

25. An apparatus for lengthening bones including at least two frame elements (12) spaced apart from one another and adapted to be mounted enclosing an elongated bone of a patient and having telescopically extendible tensioning elements (16) connected to the frame elements and securing the elements to each other in position relative to one another and having fixation elements (14) adapted to be secured to the frame elements and adapted to transfix the bone of a patient approximately perpendicular to its long direction, the improvement comprising each of said frame elements (12) having a generally U-shaped configuration and having at least two adjacent rows (18, 18') of elongated slots (20, 20', 20"), said fixation elements (14) and said tensioning elements (16) being adapted for securement to said frame elements at said slots, wherein said elongated slots (20, 20', 20") are interrupted by at least one transverse slot (22).

26. An apparatus for lengthening bones including at least two frame elements (12) spaced apart from one another and adapted to be mounted enclosing an elongated bone of a patient and having telescopically extendible tensioning elements (16) connected to the frame elements and securing the elements to each other in position relative to one another and having fixation elements (14) adapted to be secured to the frame elements and adapted to transfix the bone of a patient approximately perpendicular to its long direction, the improvement comprising each of said frame elements (12) having a generally U-shaped configuration and having at least two adjacent rows (18, 18') of elongated slots (20, 20', 20"), said fixation elements (14) and said tensioning elements (16) being adapted for securement to said frame elements at said slots, wherein said U-shaped element has at least one free end and wherein at least one elongated slot (20") is located at said free end of the U-shaped frame element (12) and is freely accessible at the free end.

* * * * *